United States Patent [19]
Heckele et al.

[11] Patent Number: 5,954,632
[45] Date of Patent: Sep. 21, 1999

[54] ENDOSCOPE IN PARTICULAR A MEDIASTINOSCOPE

[75] Inventors: Helmut Heckele, Knittlingen; Martin Weigel, Maulbronn-Schmie, both of Germany; Marcel Dahan, Toulouse, France; Albert Linder, Leonberg-Höfingen, Germany

[73] Assignee: Richard Wolf GmbH, Knittlingen, Germany

[21] Appl. No.: 09/076,982

[22] Filed: May 13, 1998

[30] Foreign Application Priority Data

May 21, 1997 [DE] Germany .......................... 197 21 138

[51] Int. Cl.⁶ ...................................................... A61B 1/04
[52] U.S. Cl. ......................... 600/104; 600/184; 600/131; 600/220; 600/221; 600/222; 600/226
[58] Field of Search ..................... 600/131, 184, 600/185, 188, 190, 196, 197, 220, 221, 222, 223, 226, 104

[56] References Cited

U.S. PATENT DOCUMENTS

| | | | |
|---|---|---|---|
| 1,568,732 | 1/1926 | Haslinger | 600/196 |
| 3,532,088 | 10/1970 | Fiore | 600/222 X |
| 4,323,057 | 4/1982 | Jamieson | 600/221 |
| 4,832,004 | 5/1989 | Heckele | 600/197 X |
| 4,905,670 | 3/1990 | Adair | 600/221 X |
| 5,363,838 | 11/1994 | George . | |
| 5,498,231 | 3/1996 | Franicevic . | |
| 5,846,249 | 12/1998 | Thompson | 600/220 X |

FOREIGN PATENT DOCUMENTS

| | | |
|---|---|---|
| 2 272 632 | 12/1975 | France . |
| 44 45 599 A1 | 9/1995 | Germany . |
| 2 210 796 | 10/1988 | United Kingdom . |
| 2258398 | 2/1993 | United Kingdom ................... 600/185 |
| WO 92/19148 | 11/1992 | WIPO . |
| WO 93/20741 | 10/1993 | WIPO . |

OTHER PUBLICATIONS

Bulletin of Karl Storz GmbH & Co. 78532 Tuttlingen "Spreizbare Operations–Laryngoskope n. Weerda" (Weerda Expandable Operation Laryngoscope) LA 18 C, LA 19 C, published Jan. 1994.

*Primary Examiner*—Jeffrey A. Smith
*Attorney, Agent, or Firm*—Panitch, Schwarze, Jacobs & Nadel, P.C.

[57] ABSTRACT

An endoscope, in particular a mediastinoscope, in which the handle and the optics guided therein form an inseparable unit and which includes a first and second spatula-like part which can be separated from one another in the longitudinal direction. An adjusting mechanism is provided which permits a separation, a fastenable displacement parallel to the axis and a fastenable pivoting of the two parts relative to one another. In particular by way of the pivotability an expansion of a body cavity to be visually examined or which is to undergo therapy by way of introduced auxiliary instruments is made possible according to requirements.

10 Claims, 4 Drawing Sheets

ENDOSCOPE IN PARTICULAR A MEDIASTINOSCOPE

BACKGROUND OF THE INVENTION

The invention relates to an endoscope, in particular a mediastinoscope with optics guided between two parts and with a handle which connects to the proximal end of the parts at an angle to the longitudinal axis and which can be releasably connected to a camera via a receiver and to a fiber-optic cable via a coupling.

An endoscope of this type is known from DE 44 45 599 A1. Here the outer shank consists of a single tube whose diameter at the distal end is broadened forming a lip projecting beyond the distal end of the shank tube.

The free lumen of the remaining operating channel which is available is determined by the diameter of the shank tube and thus cannot be changed with regard to space. Thus the operator in the operating channel only has a limited and unchangeable space available so that on application of several instruments, the handling thereof and the view through the remaining free space into the body cavity is under certain circumstances considerably limited.

Indeed endoscopic operations in certain body cavities require, apart from a good handling ability of the auxiliary means, a large as possible free space which where necessary can also be adapted to the anatomical circumstances in order to be able to introduce various auxiliary instruments through the operating channel into the body cavity to be treated or to be examined.

BRIEF SUMMARY OF THE INVENTION

It is therefore the object of the invention to provide an endoscope, in particular a mediastinoscope whose handling for the operator with reduced costs is further improved and which makes possible an operating channel which is changeable in its spacial extension, and at the same time an optimal visual control on applying several instruments.

The above object is achieved with such a type of endoscope in that the handle and optics form an inseparable unit, that the optics are guided within the two parts along the inner surface of the one part, that the parts consist of a first and second spatula-like part separated from one another in the longitudinal direction and that there are provided adjusting means which permit a separation, a fastenable displacement parallel to the axis and a fastenable pivoting of the two parts to one another.

By way of this design formation of the endoscope according to the invention, with the two spatula-like parts, by way of a parallel displacement and/or pivoting of these two parts to one another the space available for the operating channel can be changed considerably. A body cavity to be visually examined or to be treated by way of introduced auxiliary instruments can on account of these adjusting possibilities be broadened to the requirements and undergo therapy with a visual control.

Since the two spatula-like parts are separable from one another, also various spatulas can be combined with one another. In a further formation of the endoscope according to the invention it is further possible also to the make the angle between the handle and the optics running parallel to the two spatulas adjustable. As such the operator is given the possibility of setting the viewing and retaining position favorable to him, by which means the visual control is made easier and premature tiring and likewise is noticeably reduced.

BRIEF DESCRIPTION OF THE DRAWINGS

Further advantageous features are to be deduced from the dependent claims and from the subsequent description of an embodiment example shown in the drawings. The drawing figures individually show:

DETAILED DESCRIPTION OF THE INVENTION

Figure 1:
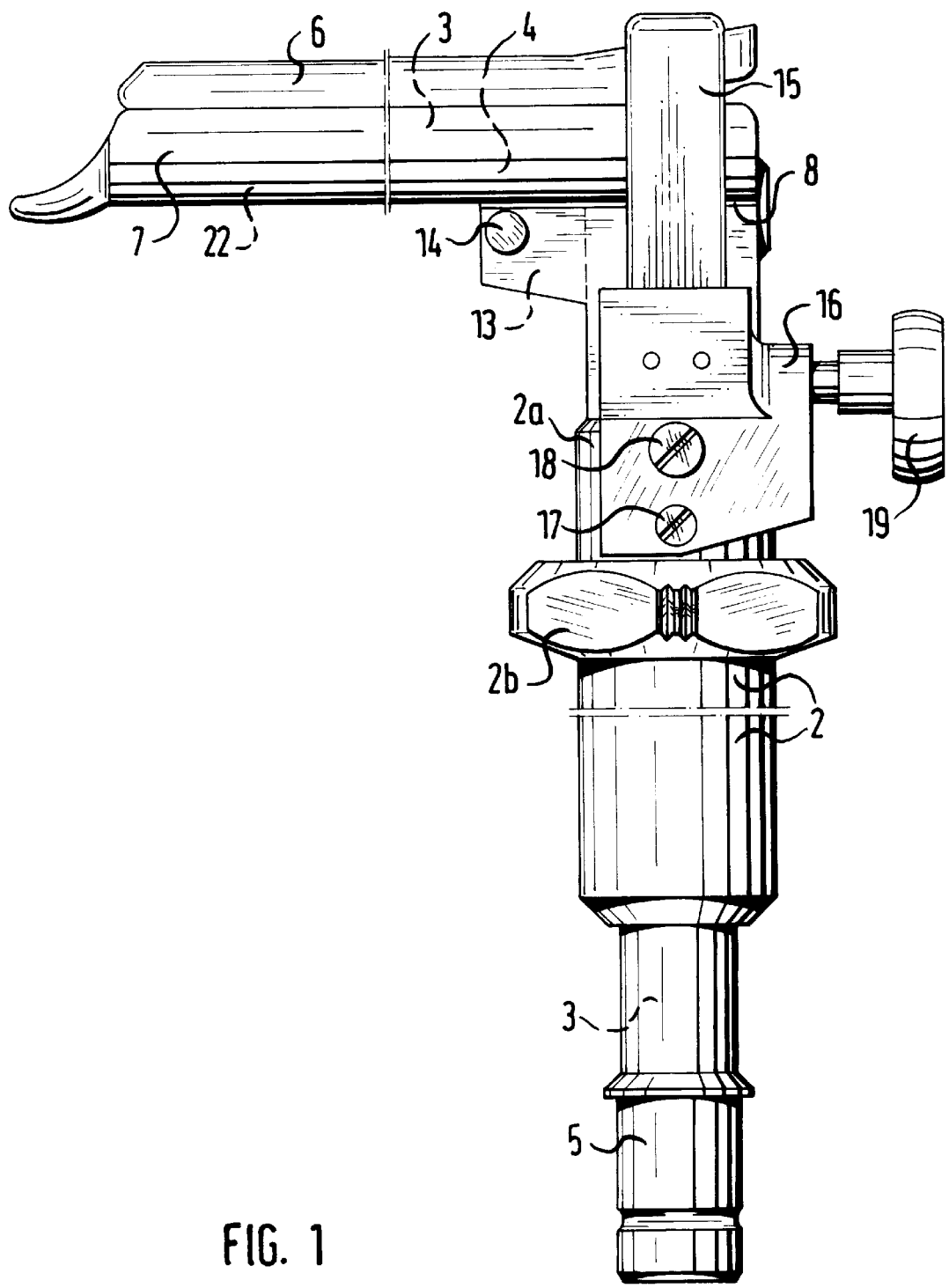
FIG. 1 a lateral view of the endoscope according to the invention with a first and second spatula arranged parallel to one another and linked to one another, FIG. 2 a view of the distal end of the endoscope according to FIG. 1 with first and second spatula-like parts located in mutual bearing, FIG. 3 a lateral view of the inseparable unit consisting of the handle and the optics, FIG. 4 a view of the distal end of the unit according to FIG. 3, FIG. 5 a plan view on the spatula-like part releasable from the handle and FIG. 6 a lateral view of the part releasable from the handle, according to FIG. 5.

The endoscope represented in FIG. 1 in a lateral complete view, which is in particular applicable as a mediastinoscope, consists of a handle 2 on whose distal end there is arranged a receiver 5 which serves the attachment of an ocular funnel, a camera or likewise (not shown) in order to be able to observe the image transmitted by way of the optics 3, 4 integrated into the handle 2 directly or on a monitor. The optics 3, 4 arranged in the handle 2 and the handle 2 together form an inseparable constructional unit. Onto the end of the handle 2, which is opposite the receiver 5 according to FIG. 1, there is fastened a first spatula-like part 6 by way of a fastening clip 15 formed with this part as one piece with a joint body 16 partly encompassing the handle 2 and connected to the handle in a pivotingly movable manner by way of a joint axis 17.

The first spatula-like part 6 on account of the above mentioned adjusting means is inseparably but pivotably connected to the handle 2. Tile pivoting angle is set by an adjusting screw 19. As will be explained further below, also by way of rotatable handle parts 2a, 2b coaxially surrounding the handle 2, on whose upper end the joint body 16 is mounted pivotingly movable through the pivoting axis 17, the first spatula-like part 6 is adjustable parallel to the longitudinal axis of the optics and thus also parallel to the second spatula-like part 7.

Figure 5:

FIG. 1 shows the second spatula-like part 7 arranged parallel to the first part 6. The inner side of the part 6 comprises a receiver 22 through which the distal end of the optics 4 can be guided with slight play. FIG. 5 shows that the second spatula-like part at its proximal end has a proximally open cutout 9 which is limited by parallel lateral surfaces 10. The cutout 9 and the lateral surfaces 10 serve, as will be explained later, for attaching and fastening the second spatula-like part 7 to the endoscope parallel to the optics 4 whose distal end is guided through the receiver 22. Furthermore the view in FIG. 2 shows a fiber-optic cable connection 23 on the handle 2, a slot 13 and a fastening screw 14 which respectively serves for accommodating and fastening the inserted second spatula-like shaft part 7.

Figure 2:
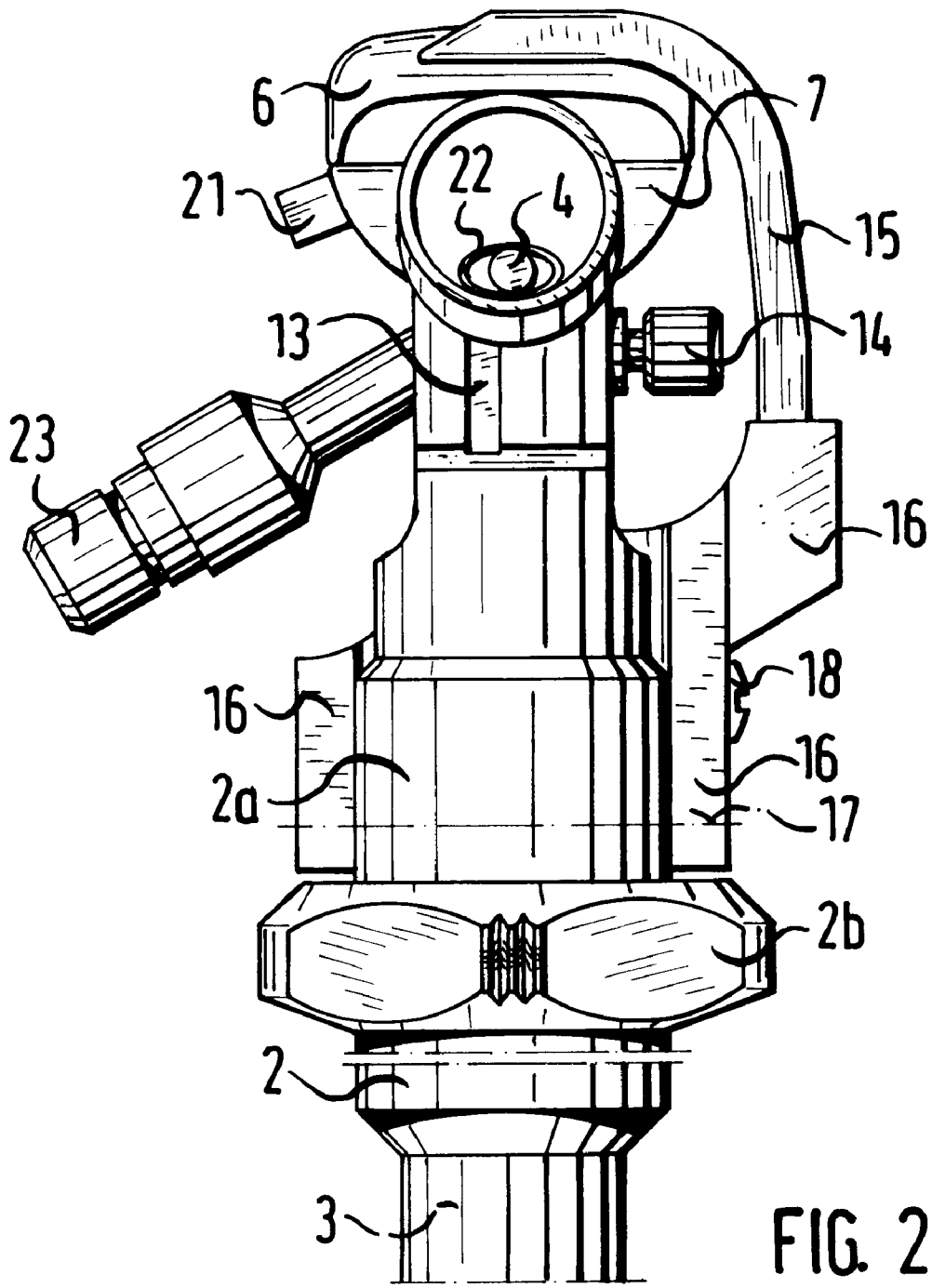

FIG. 2 shows details of the endoscope shown completely in FIG. 1, from the distal end, whereby the fastening clip 15 releasably connecting the first spatula-like part 6 to the joint body 16 can be particularly clearly recognized.

The second spatula-like part 7 is in FIG. 2 fixed in its assembled condition by way of the fastening screw 14 and runs parallel to the optics 4. The joint body 16 is adjusted by way of the adjusting screw 19 such that the first spatula-like part 6 stands roughly parallel to the second spatula-like part 7. The rotatable handle parts 2a, 2b on the handle 2 are set such that the the first spatula like part 6 bears on the second spatula-like part 7 without any distance to this.

Figure 4:
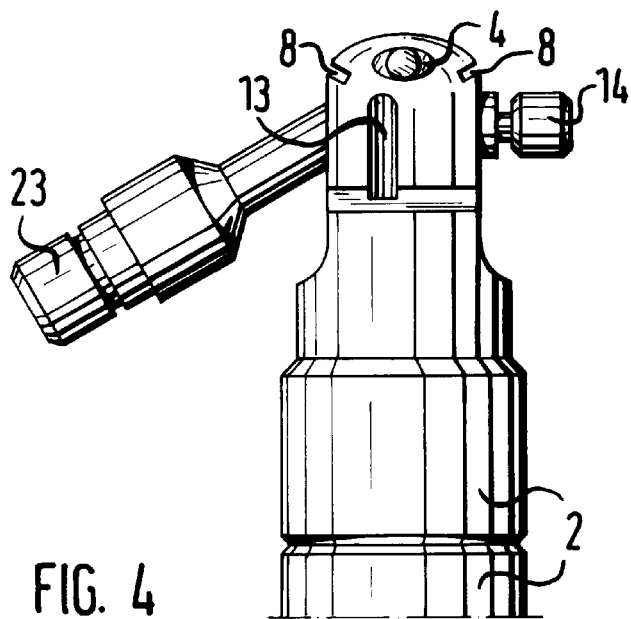
Figure 6:
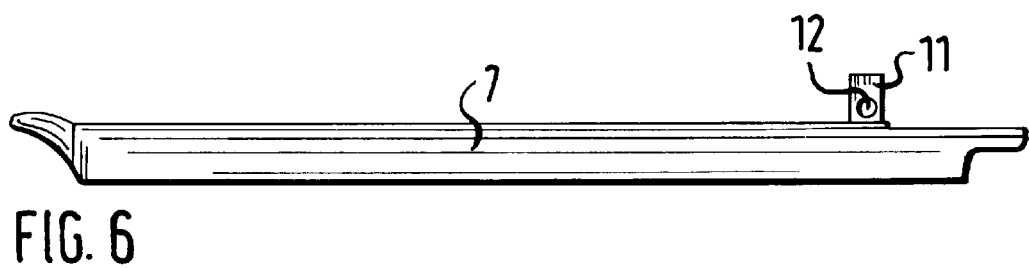

FIG. 4 further shows the two receiving slots 8 which serve the accommodation of the second part 7. These slots 8 run parallel on the end face of the handle 2 over its whole length and are formed such that they tightly accommodate the lateral surfaces 10 limiting the cutout 9 of the second part.

Figure 3:
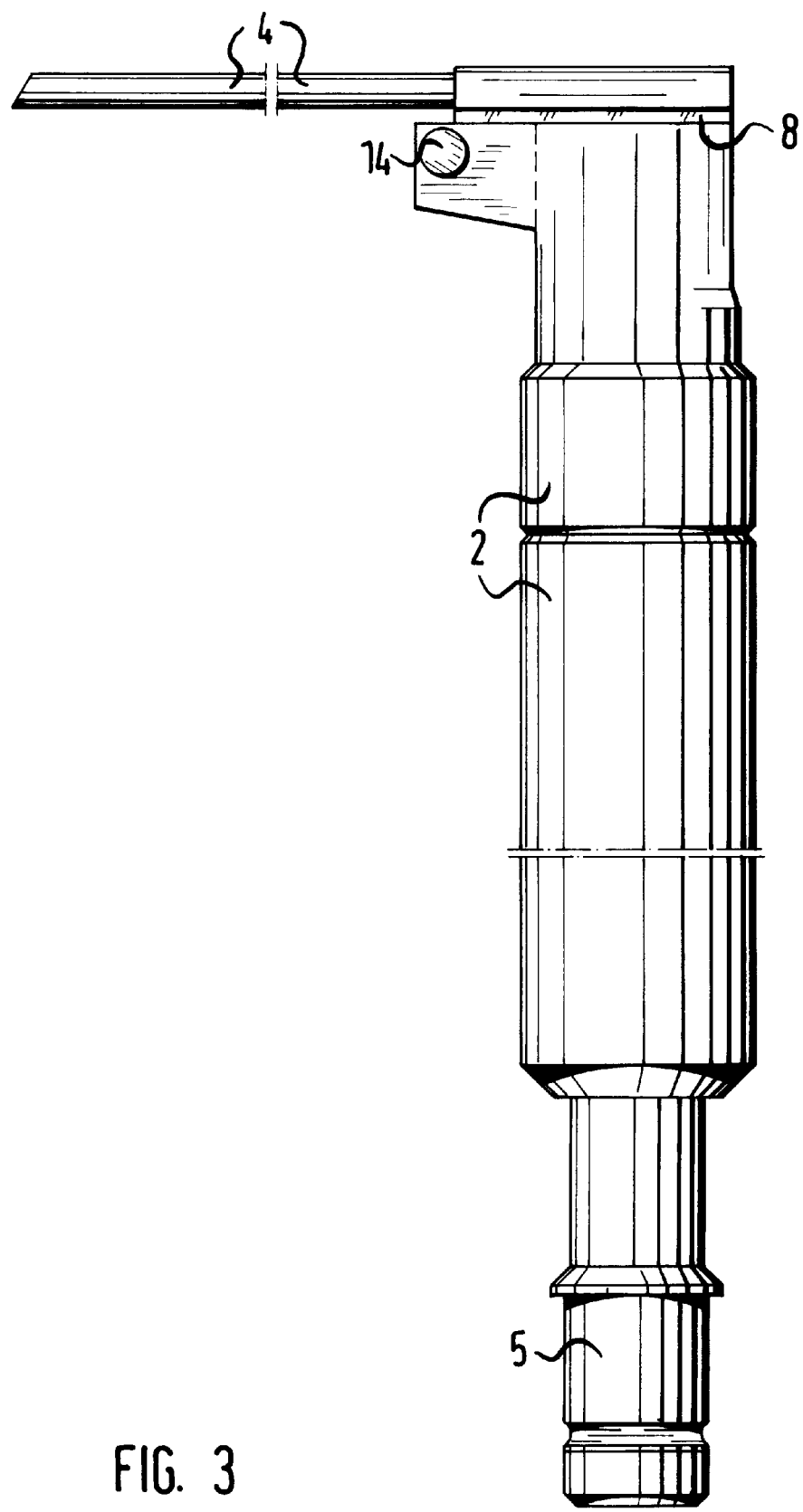

FIGS. 3 and 4 clearly show the receiving and fastening means for accommodating and fastening the removable second part 7. The latter is inserted into the receiving slots 8. The second part 7 comprises on its convex outer side a fastening bracket 11 with a conical bore 12, and as a fastening means on the handle 2 there serves a fastening screw 14 with a conical shoulder which, when the fastening bracket 11 is located in the receiving slot 13 attached to the handle 2, engages into the bore 12 and by way of this unmovably fixes the second part 7.

This condition is shown in FIGS. 1 and 2, wherein the first spatula-like part is adjusted bearing sealingly on the second spatula-like part by way of the handle parts 2a, 2b provided on the handle 2.

In order to be able to adjust the handle parts 2a, 2b on the handle, there is located on the handle part 2a an outer thread and on the handle part 2b an inner thread, so that both handle parts can be adjusted along the cylinder longitudinal axis of the handle and thus the first part 6 parallel to the second part 7.

In FIG. 1 there can be recognized one of two joint pins 17 which form a pivoting axis on the joint body 16 and engage into the handle 2. Furthermore there is attached on the joint body 16 a ball latch 18 with which the two parts 6 and 7 proceeding from a position parallel to the axis, can be releasably fixed in several pivoting positions to one another. If it is necessary to widen the body opening to be examined to a certain degree, then this may be effected by pivoting out at least one of the two shank parts 6, 7.

For fixing auxiliary instruments to be guided within the two parts 6, 7 or outside of these, the two parts 6, 7 at their concave inner side and/or their convex outer side as shown in FIG. 2 may comprise one or several guiding receivers 21 for accommodating auxiliary instruments.

It must still be mentioned that the endoscope according to the invention, although this is not shown in the figures, may comprise means for adjusting the angle between the receiver 5 and the cylinder longitudinal axis of the handle 2.

As a whole the invention permits an endoscope, in particular a mediastinoscope, to comprise the following advantageous features:

The optics run parallel to the spatula axis along the removable second part 7 and are rigidly attached to the handle so that the optics and handle form one unit. The second part 7 guiding the optics may be separated from the handle.

Both spatula-like parts 6,7 may be spread and additionally also adjusted parallely. Indeed the pivoting of the two parts permits an expansion of a body cavity to be visually controlled or which is to undergo therapy by way of introduced auxiliary means according to the requirements of the operator. At the same time with this the handling is also simplified since the two distal ends of the first and second parts bearing on the body cavity walls are locally fixed.

By way of the fact that a part, more specifically the second part 7 is separable from the endoscope, differing spatula-like parts may be combined with one another. For example the radius of curvature, the length and shape of the second part may be changed. The outer edges of the second part 7 may run conically, so that this tapers distally. At the distal end the second part 7 may also comprise an atraumatic rounded lip projecting beyond the distal end of the endoscope. The optics have a standard interface, by which means it is ensured that an attached camera may also be used in another way.

It is also advantageous that at the proximal end of the handle 2 there is located only the ocular funnel or a part of the optics accommodating a camera. With this the operator is offered the possibility of examining the body cavity directly through the eyepiece or also of directly visually monitoring the endoscopic operation in the body cavity.

By way of the optionally present adjustability of the angle between the receiver and the longitudinal axis of the handle 2 the operator is given the possibility of setting the viewing and retaining position which is most favorable for him, by which means the viewing is simplified and additionally, appearances of tiredness and likewise are considerably reduced.

We claim:

1. A mediastinoscope, comprising a handle having a longitudinal axis, first and second parts each having a proximal end and being connected with the handle at the proximal ends at an angle to the longitudinal axis of the handle, optics located between the two parts and extending through the handle which are releasably connectable to a camera via a receiver and to a fiber-optic cable via a coupling, the optics between the first and second parts being located along an inner surface of the first part, the first and second parts being spatula-shaped and being separated from one another in a longitudinal direction, and adjusting means which permit a separation, a fastenable displacement parallel to the longitudinal axis and a fastenable pivoting of the two parts relative to one another.

2. A mediastinoscope according to claim 1, wherein the first part includes a fastening clip formed with it as one piece, and is unreleasably connected by the fastening clip to a joint body which partly encompasses the handle, the first part being connected to the joint body in a pivotingly movable manner by a joint axis.

3. A mediastinoscope according to claim 2, wherein a screw is engaged on the handle below the pivoting axis of the joint body, the screw permits pivoting of the first part fastened to the joint body.

4. A mediastinoscope according to claim 2, wherein the joint body is displaceable in a direction of the longitudinal axis on the handle so that the first part is also adjustable perpendicularly to the second part.

5. A mediastinoscope according to claim 2, wherein a ball latching element is mounted on the joint body which is adapted to fix a position of the first part relative to the second part.

6. A mediastinoscope according to claim 1, wherein an elongate cutout with parallel lateral surfaces is located at the proximal end of the second part and the handle includes an end face having two parallel slots which extend across a width of the handle, and the two parallel lateral surfaces of the cutout can be introduced into the two parallel slots.

7. A mediastinoscope according to claim 6, wherein the second part includes an outer side having a fastening bracket with a bore therethrough which borders on the cutout, and the handle includes a slot arranged parallel to the longitudinal axis and an adjusting screw parallel thereto, the fastening bracket being located in the slot and fastened by the adjusting screw engaged into the bore.

8. A mediastinoscope according to claim 1, wherein the second part includes an inner side which comprises a receiver, a distal end of the optics being guided through the receiver.

9. A mediastinoscope according to claim 1, wherein the angle between a longitudinal axis of the of the optics and the longitudinal axis of the handle is 90°.

10. A mediastinoscope according to claim 1, wherein the angle between a longitudinal axis of the optics and the longitudinal axis of the handle is adjustable.

* * * * *